(12) United States Patent
Wheeler

(10) Patent No.: US 6,441,051 B1
(45) Date of Patent: Aug. 27, 2002

(54) INSECT ERADICATOR AND METHOD

(76) Inventor: William B. Wheeler, PO Box 1188, Concord, NC (US) 28026

( * ) Notice: Subject to any disclaimer, the term of this patent is extended or adjusted under 35 U.S.C. 154(b) by 0 days.

(21) Appl. No.: 09/955,891

(22) Filed: Sep. 20, 2001

(51) Int. Cl.$^7$ .................. A01N 35/00; A01N 25/00; A61K 31/12
(52) U.S. Cl. ......................... 514/675; 424/405
(58) Field of Search ................... 514/675; 424/405

(56) References Cited

U.S. PATENT DOCUMENTS

| | | | | |
|---|---|---|---|---|
| 4,915,707 A | * | 4/1990 | Whitworth | 44/62 |
| 5,308,365 A | * | 5/1994 | Kesling et al. | 44/447 |
| 5,316,558 A | * | 5/1994 | Gonzalez | 44/340 |

FOREIGN PATENT DOCUMENTS

| | | | |
|---|---|---|---|
| DE | 2520971 | * | 11/1976 |
| DE | 19620891 | * | 11/1997 |
| GB | 1483186 | * | 8/1977 |
| GB | 2033421 | * | 5/1980 |
| JP | 57125752 | * | 8/1982 |
| RU | 2025064 | * | 12/1994 |

OTHER PUBLICATIONS

Material Safety Data Sheet for Florida Chemical Company from Worth Chemical dated Oct. 5, 1998; for product name D–Limonene. 4 pages.

Material Safety Data Sheet from Hoechst Celanese for product name Genapol DA–060 (polyglycol ether); date printed Sep. 26, 1996; 4 pages.

Material Safety Data Sheet for Product Name Stepantex DA–6 (Product Class) Alcohol Ethoxylate) dated Apr. 7, 1994; 5 pages.

Material Safety Data Sheet for Diacetone Alcohol date prepared—Jan. 26, 1998, date printed Jun. 27, 2000—7 pages.

Printout from Columbus Foods Company for Soy Methyl Ester dated Dec. 1, 2000; 6 pages.

* cited by examiner

Primary Examiner—Alton Pryor

(57) ABSTRACT

An effective, environmentally, friendly insecticide and method of application are described herein. The conventional insecticide d-limonene is combined with diacetone alcohol to enhance its lethal properties. An emulsion concentrate is first prepared using d-limonene, diacetone alcohol, polyglycol ether and methyl soyate. This concentrated emulsion mixture can then be stored for use as needed. When needed this concentrated emulsion is mixed at a ratio of 10 parts by weight emulsion and 90 parts by weight of water to form an effective mixture for spraying in a modified manual garden sprayer having two spray wands.

16 Claims, 2 Drawing Sheets

INSECT ERADICATOR AND METHOD

FIELD OF THE INVENTION

The invention herein pertains to insecticides, and particularly pertains to an insecticide and method of application for killing fire ants.

DESCRIPTION OF THE PRIOR ART AND OBJECTIVES OF THE INVENTION

Arsenic and other metals have been used for many years in insecticides as have other chemicals which are hazardous and/or unfriendly to the environment. Governments and other agencies in recent years, have encouraged the use of less toxic or environmentally friendly insecticides and d-limonene has been touted as meeting this criteria. D-limonene thus has been used as the active ingredient in various insecticide mixtures for killing ants and the like at about a 5% concentration. However, as such the kill rate is only approximately 70% after twenty-four hours. Surviving fire ants and other similar insects will flee the treated mounds and areas and, in a matter of a few days, begin rebuilding their colony at a new location. Thus, as one hill is eradicated the 30% or so ants which are not fatally affected will migrate to another location, requiring yet further insecticide applications as the cycle repeats and the problems persist.

Thus, with the difficulties and disadvantages of known insecticides, the present invention was conceived and one of its objectives is to provide an insecticide which is both environmentally friendly and which has an extremely high kill rate.

It is yet another objective of the present invention to provide an insecticide mixture which utilizes d-limonene and diacetone alcohol in an effective synergistic ratio.

It is still another objective of the present invention to provide an insecticide which is both safe to handle and easy to apply.

It is also another objective of the present invention to provide an effective met hod for killing f ire ants using a portable sprayer having two spray wands for simultaneous spraying to thus prevent multiple (subsequent) insecticide applications.

Various other objectives and advantages of the present invention will become apparent to those skilled in the art as a more detailed description is set forth below.

SUMMARY OF THE INVENTION

The aforesaid and other objectives are realized by providing an insecticide mixture in the form of an emulsion concentrate which can be diluted for spraying from a modified portable manual garden sprayer having two wands. The concentrated emulsion mixture is prepared by combining by weight:

50 parts of d-limonene;
25 parts of diacetone alcohol;
15 parts of polyglycol ether; and
10 part of methyl soyate.

In a suitable container this mixture is stirred sufficiently to form an emulsion concentrate which can be stored for dilution for later use.

When needed, 10 parts by weight of the emulsion concentrate is placed into a modified, hand pressurized garden sprayer having two hoses and wands. Ninety (90) parts by weight of water are then added and mixed by agitation. The diluted emulsion can then be sprayed for an effective insecticide through the wands simultaneously onto an ant hill or the like.

The method of applying the insecticide mixture described above from the garden sprayer includes the following steps: one wand is used to first penetrate an insect mound such as an ant hill and the insecticide mixture is then dispensed along the bottom thereof. Simultaneously therewith, the second wand sprays the outer surface of the ant hill with the mixture to saturate the same.

It has been found that after two hours all visible signs of life are absent and the ant hill remains inactive at subsequent checks, some twenty-four hours later, verifying the estimated 100% kill rate.

DETAILED DESCRIPTION OF THE PREFERRED EMBODIMENTS AND OPERATION OF THE INVENTION

Figure 3:
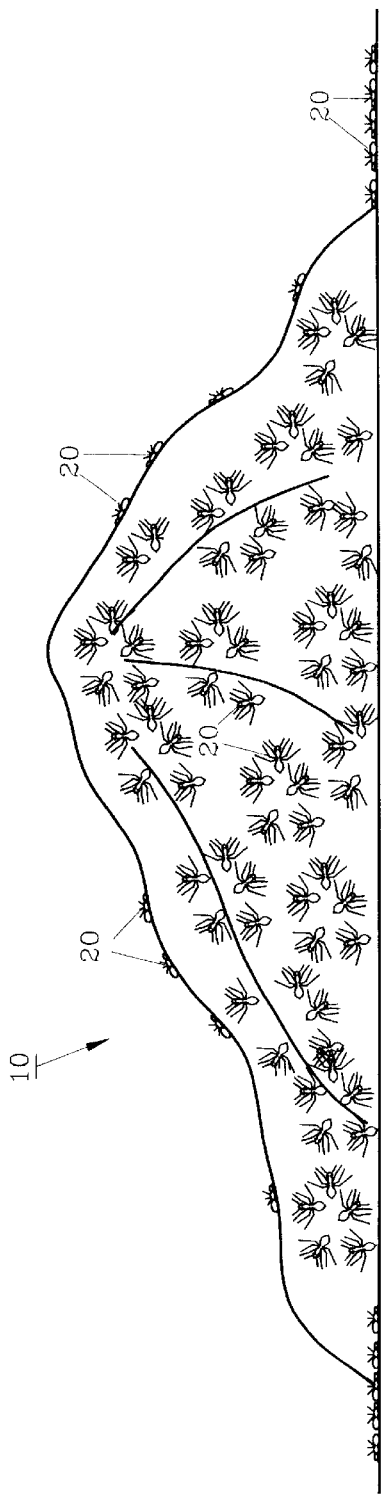
FIG. 3 shows the results of the ant hill about two hours after the application.
Figure 1:
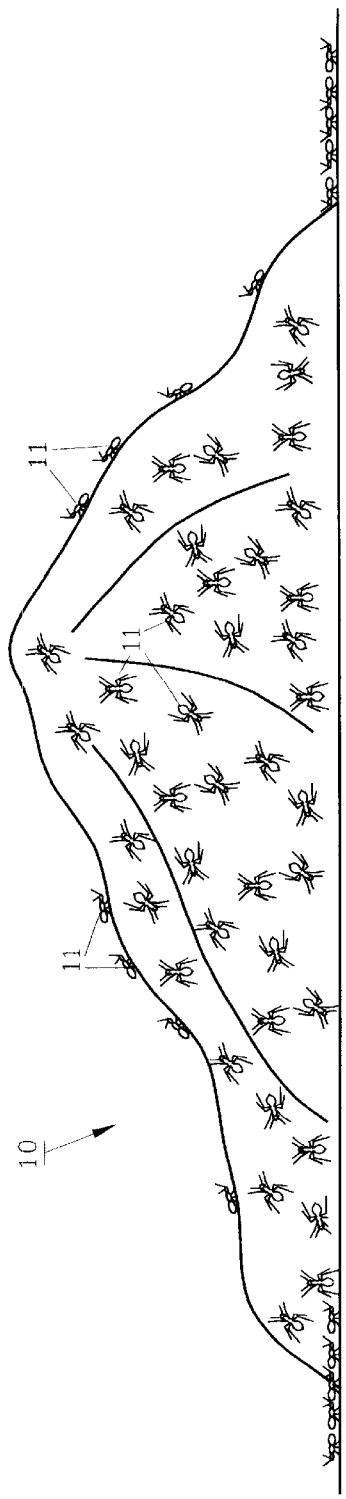
FIG. 1 illustrates a typical ant hill as built by fire ants.
Figure 2:
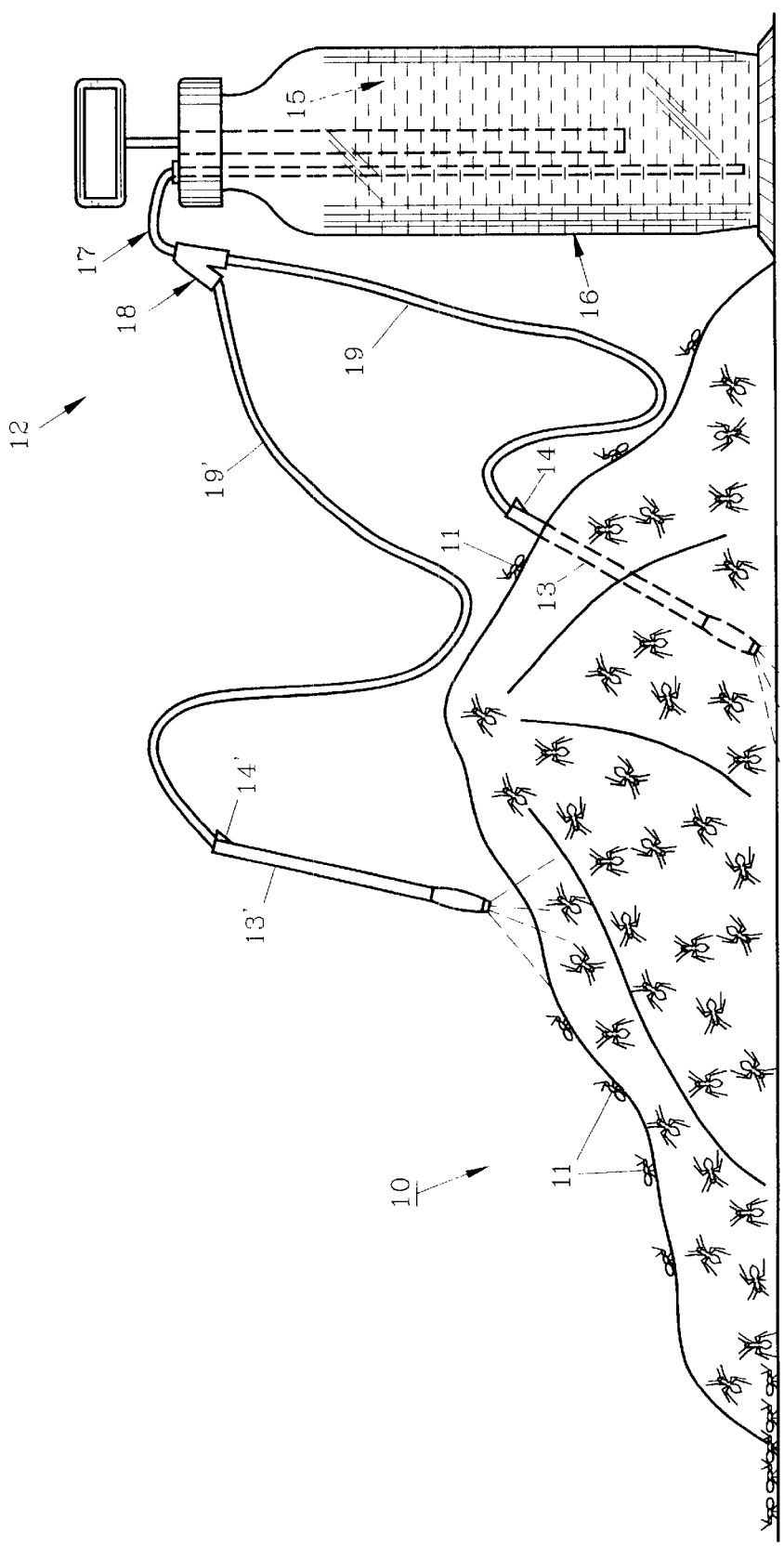
FIG. 2 shows the ant hill with the two wands of the modified portable garden sprayer applying insecticide along the bottom and outer surface thereof.

For a better understanding of the invention and its operation, turning now to the drawings, the preferred method of eradicating insects is shown in FIGS. 1–3. In FIG. 1, a typical ant hill 10 which may have a height of six inches (15.24 cm) and a base diameter of approximately 12–18 inches (30.48–45.72 cm) as constructed by either migratory or native fire ants. Such ant hills are present in fields, pastures, lawns and other areas which are infrequently mowed, tilled, cultivated or the like. Thousands of fire ants can be present at any time which and are referred to as a "colony" having one or more queens, workers and other designations.

A typical garden sprayer 12 seen in FIG. 2 has been modified by adding usual Y-fitting 18 to flexible hose 17. This allows for hoses 19, 19' to connect to Y-fitting 18 which accommodates respectively wands 13, 13'. Spray container 16 is filled with, for example a two and one-half gallon mixture 15 made from preferred insect eradicator emulsion mixture in concentrated form consisting of:

1. 50 parts by weight of d-limonene;
2. 25 parts by weight of diacetone alcohol;
3. 15 parts by weight of decyl alcohol having 6 moles of ethylene oxide (polyglycol ether); and
4. 10 parts by weight of methyl soyate.

This preferred mixture is blended at ambient temperatures such as with an electric mixer to form a concentrated emulsion.

Next, 100 parts by weight of the eradicator emulsion as prepared above are then placed in garden sprayer 12 (FIG. 2) and 900 parts by weight of water are added to form diluted emulsion mixture 15. Diluted mixture 15 is then stirred by hand, and garden sprayer 12 is then closed and pressurized as by manual pumping. With garden sprayer 12 placed nearby, wand 13 of garden sprayer 12 is inserted in or near the bottom of ant hill 10 having live ants 11 as seen in FIG. 2 and trigger 14 of wand 13 is depressed, causing mixture 15 within tank 16 to be directed along the bottom of ant hill 10. Simultaneously therewith, the top of ant hill 10 is sprayed as also shown in FIG. 2 using wand 13' and trigger 14'. As would be understood, one hand would hold wand 13 whereas the other hand would hold wand 13'. Once the upper surface of hill 10 has been saturated with mixture 15, triggers 14, 14' are released and spraying ceases. Such treatment generally has a very effective kill rate within two hours and a total, 100% kill rate within twenty-four hours as seen by dead fire ants 20 in FIG. 4.

Studies in the past have determined that d-limonene is an effective pesticide for fire ants with a kill rate of approximately 70% after twenty-four hours at a 5%. concentration. The present invention utilizes diacetone alcohol in combination with d-limonene to enhance the lethal power of d-limonene while providing an environmentally friendly insecticide or eradicator. Diacetone alcohol is utilized preferably at a ratio by weight of approximately one-half that of d-limonene. This combination provides a 100% kill rate after twenty-four hours when d-limonene is used at about 5% concentration as seen in the method described above. Decyl alcohol acts as a leveling agent in the mixture, while methyl soyate is an effective emulsifying agent.

Other alcohols have been tried but do not compare in effectiveness to the diacetone alcohol when used in combination with d-limonene.

The illustrations and examples provided herein are for explanatory purposes and are not intended to limit the scope of the appended claims.

I claim:

1. An insect eradicator consisting essentially of a mixture of d-limonene, diacetone alcohol and decyl alcohol having six moles of ethylene oxide.

2. The mixture of claim 1 wherein said d-limonene is two parts by weight and said diacetone alcohol is one part by weight.

3. An insect eradicator emulsion comprising by weight:
   50parts of d-limonene;
   25parts of diacetone alcohol;
   15parts of decyl alcohol having 6 moles of ethylene oxide); and
   10 parts methyl soyate.

4. The insect eradicator as claimed in claim 3 wherein said d-limonene has a boiling point of 310° F. and a specific gravity at 25° C. of 0.838–0.845.

5. The insect eradicator of claim 3 wherein said diacetone alcohol has a molecular weight of 116.2 and a boiling point of 145° to 172.2° C. at 760 mmHg.

6. The insect eradicator of claim 3 wherein said decal alcohol is a polyglycol ether having refraction index of 1.462 at 60° C.

7. The insect eradicator of claim 3 wherein said methyl soyate has a boiling point of 200° C. at 760 mmHg and a specific gravity of 0.87 at 25° C.

8. The insect eradicator of claim 3 further comprising by weight 900 parts of water.

9. A method of eradicating insects comprising the steps of:
   a) locating an insect colony,
   b) applying a mixture off methyl soyate d-limonene, diacetone alcohol and decyl alcohol having six moles of ethylene oxide to the insect colony to kill the same.

10. The method of claim 9 wherein locating an insect colony comprises the step of locating an ant colony.

11. The method of claim 9 wherein applying a mixture comprises the steps of applying an emulsion mixture comprising;
   a) 50 parts by weight of d-limonene;
   b) 25 parts by weight of diacetone alcohol;
   c) 15 parts by weight of decyl alcohol having six moles of ethylene oxide;
   d) 10 parts by weight of methyl soyate; and
   e) 900 parts by weight of water.

12. The method of claim 11 further comprising the step of spraying the mixture on the insect colony.

13. The method of claim 12 further comprising the step of spraying an ant hill with the mixture.

14. The method of claim 13 further comprising the step of spraying along the inside bottom of the ant hill while simultaneously spraying on the outer surface of the ant hill.

15. An insect eradicator comprising a mixture of di-limonene, diacetone alcohol, methyl soyate, and decyl alcohol having six moles of ethylene oxide.

16. A method of eradicating insects consisting essentially of the steps of:
   a) locating an insect colony,
   b) applying a mixture of d-limonene, diacetone alcohol, and decyl alcohol having six moles of ethylene oxide to the insect colony to kill the same.

* * * * *